United States Patent
Szabo et al.

(10) Patent No.: US 9,427,216 B2
(45) Date of Patent: Aug. 30, 2016

(54) SYSTEMS AND METHODS FOR CLOSING A VESSEL WOUND

(75) Inventors: David Szabo, Doylestown, PA (US); Jonathan Gabel, Randolph, NJ (US); Roddi Simpson, Watchung, NJ (US); Benjamin Wicks, Huntington (GB); David Gale, Cambridge (GB)

(73) Assignee: Cardinal Health Switzerland 515 GmbH (CH)

( * ) Notice: Subject to any disclaimer, the term of this patent is extended or adjusted under 35 U.S.C. 154(b) by 1629 days.

(21) Appl. No.: 11/317,479

(22) Filed: Dec. 23, 2005

(65) Prior Publication Data

US 2007/0149999 A1 Jun. 28, 2007

(51) Int. Cl.
*A61B 17/08* (2006.01)
*A61B 17/00* (2006.01)

(52) U.S. Cl.
CPC ...... *A61B 17/0057* (2013.01); *A61B 17/00491* (2013.01); *A61B 2017/00637* (2013.01); *A61B 2017/00654* (2013.01)

(58) Field of Classification Search
CPC .............. A61B 17/0057; A61B 17/00491; A61B 2017/00654; A61B 2017/00637
USPC .............. 606/213, 214; 604/103.01
See application file for complete search history.

(56) References Cited

U.S. PATENT DOCUMENTS

| | | | |
|---|---|---|---|
| 4,364,392 A * | 12/1982 | Strother et al. | 606/195 |
| 5,213,576 A | 5/1993 | Abiuso et al. | |
| 5,282,827 A | 2/1994 | Kenssey et al. | |
| 5,324,306 A | 6/1994 | Makower et al. | |
| 5,342,393 A * | 8/1994 | Stack | 606/213 |
| 5,354,271 A | 10/1994 | Voda | |
| 5,370,660 A * | 12/1994 | Weinstein et al. | 606/215 |
| 5,383,896 A | 1/1995 | Gershony et al. | |
| 5,391,183 A | 2/1995 | Janzen et al. | |
| 5,413,571 A * | 5/1995 | Katsaros et al. | 606/213 |
| 5,441,517 A | 8/1995 | Kensey et al. | |
| 5,645,566 A | 7/1997 | Brenneman et al. | |

(Continued)

FOREIGN PATENT DOCUMENTS

| | | |
|---|---|---|
| JP | 2005-000683 A | 1/2005 |
| WO | WO 98/11830 A1 | 3/1998 |

(Continued)

OTHER PUBLICATIONS

Weisel, J. W., "The Mechanical Properties of Fibrin for Basic Scientists and Clinicians", Biophysical Chemistry, vol. 112 (2004) pp. 267-276.

(Continued)

*Primary Examiner* — Gregory Anderson
*Assistant Examiner* — Son Dang (57) ABSTRACT

Vessel wound closure systems and method for sealing a puncture wound in a target vessel, such as those puncture wounds that occur from interventional procedures. The vessel wound closure system comprises at least a biocompatible, viscoelastic, self-sealing septum material injected onto the adventitia of the target vessel prior to performance of an interventional procedure. The prior injected septum material remains and seals the puncture wound of the target vessel even after various components associated with accessing the target vessel and the performance of the interventional procedure are removed from the target vessel and the puncture wound.

12 Claims, 10 Drawing Sheets

(56) References Cited

U.S. PATENT DOCUMENTS

| | | | |
|---|---|---|---|
| 5,662,681 | A | 9/1997 | Nash et al. |
| 5,690,674 | A * | 11/1997 | Diaz ............................ 606/213 |
| 5,741,223 | A | 4/1998 | Janzen et al. |
| 5,792,152 | A | 8/1998 | Klein et al. |
| 5,868,778 | A | 2/1999 | Gershony et al. |
| 6,033,427 | A | 3/2000 | Lee |
| 6,050,986 | A | 4/2000 | Hektner |
| 6,152,943 | A | 11/2000 | Sawhney |
| 6,238,412 | B1 * | 5/2001 | Dubrul et al. ................ 606/200 |
| 6,475,182 | B1 * | 11/2002 | Hnojewyj et al. ............. 604/82 |
| 6,733,515 | B1 * | 5/2004 | Edwards et al. ............. 606/214 |
| 6,899,889 | B1 | 5/2005 | Hnojewyj et al. |
| 7,335,220 | B2 * | 2/2008 | Khosravi et al. ............ 606/213 |
| 2004/0006352 | A1 | 1/2004 | Nobles et al. |
| 2004/0267308 | A1 * | 12/2004 | Bagaoisan et al. .......... 606/213 |

FOREIGN PATENT DOCUMENTS

| | | |
|---|---|---|
| WO | WO 2005/063129 A | 7/2005 |
| WO | 2005/074814 A2 | 8/2005 |

OTHER PUBLICATIONS

Chinese Office Action dated Feb. 5, 2010 together with English language translation.

English language translation of Notification of Reasons for Refusal dated Jan. 10, 2012 issued in Japanese Patent Application No. 2008-547336.

European Search Report dated Dec. 7, 2009, for corresponding Patent Application No. 06 839 377.6-2310.

* cited by examiner

SYSTEMS AND METHODS FOR CLOSING A VESSEL WOUND

BACKGROUND OF THE INVENTION

1. Field of the Invention

The invention generally relates to vessel wound closure techniques. More particularly, the invention relates to systems and methods for sealing puncture wounds in a blood vessel such as those that result from certain interventional procedures.

2. Related Art

A large number of therapeutic and diagnostic procedures involve the percutaneous introduction of instrumentation into a blood vessel, for example, percutaneous transluminal coronary angioplasty (PTCA). Such procedures most often involve accessing an intended site through the femoral artery. Ideally, closing and healing of the resultant vascular puncture wound successfully completes the procedure.

Traditionally, the application of external pressure to the skin at the entry site of the instrumentation into the patient has been employed to stem bleeding from the wound. A nurse or physician, for example, applies pressure to the wound site until clotting and tissue rebuilding has occurred sufficiently to seal the perforation. In some situations, the external pressure is maintained for an hour or more, during which time the patient is uncomfortably immobilized. Thus patient comfort and physician efficiency are impaired where such external pressure techniques are employed.

Additionally, the risk of hematoma exists while bleeding from the vessel occurs. Such hematoma risk continues until sufficient clotting of the wound site occurs. Moreover, external pressure devices, such as femoral compression systems, are often unsuitable for some patients, such as those with substantial amounts of subcutaneous adipose tissue, as the skin surface may be a considerable distance away from the vasculature puncture site. Inaccurate skin compression, and thus less effective wound healing, tends to occur as a result.

U.S. Pat. No. 5,383,896 to Gershony, et al. discloses a device that applies pressure to a puncture site internally for a limited period of time, after which the device is removed. The device in Gershony includes a shaft with an expandable balloon and a guidewire tip at its distal end. The distal end of the device is introduced into a blood vessel through an introducer sheath that is typically used in percutaneous interventional procedures. The balloon is then inflated and withdrawn until the balloon hemostatically engages the inner surface of the blood vessel, after which the introducer sheath is removed. A fixation collar on the shaft applies tension to the balloon for a medically sufficient time and thereafter the balloon is deflated and the entire device is removed from the body.

U.S. Pat. No. 5,645,566 to Brenneman, et al. discloses a device that applies pressure to the outside wall of a punctured blood vessel from a distance using a balloon, a sheet and a foam pad. The pressure applying device is located using a balloon in the vessel (similar to that of Gershony) and a radiopaque marker.

PCT Application WO 98/11830, published Mar. 26, 1998, S. Barak, Inventor, discloses various embodiments of an apparatus for hemostasis. Among them is a device that positions an anchor against an inner surface of an artery wall and a balloon outside the wall. The balloon is inflated to pinch the artery wall, after which the anchor is withdrawn. The balloon is maintained against the puncture until hemostasis is achieved. The anchor and balloon are removed after hemostasis is achieved.

Other arterial closure devices include bioabsorbable materials intended to remain in the body until they are absorbed as in related U.S. Pat. Nos. 5,282,827 and 5,441,517, which disclose an anchor inserted into a vessel and urged against an inner wall of the vessel as a collagen plug is deployed externally of the puncture site to expand and fill the tissue tract leading to the puncture site. A filament attaches the plug to the anchor and moves the plug and anchor relative to one another in pulley-like fashion to effect a seal at the puncture site. After emplacement, a tamping member may be used to urge the plug against the external puncture site to help seal the same.

U.S. Pat. No. 5,662,681 discloses an arterial closure device in which an anchor and plug are attached to one another via a filament. The anchor is inserted into the vessel and urged against the interior wall of the vessel as the plug is urged against the exterior wall of the vessel at a puncture site. A separate locking means moves the plug and anchor relative to one another to maintain the plug and anchor in sealing position at the puncture site.

U.S. Pat. No. 5,391,183 to Janzen, et al. describes a device that inserts hemostatic material through a tissue channel and against the outside wall of the vessel around the puncture site.

U.S. Pat. No. 5,690,674 to Diaz discloses a biodegradable plug that has two substantially parallel disks joined at their centers by a waist. The plug is positioned so that the distal disk is on the interior wall of the blood vessel, the proximal disk is on the exterior wall, and the waist is in the wound of the vessel wall.

Another known closure device includes U.S. Pat. No. 5,741,223 to Janzen, et al. This '223 patent discloses the placement of a plug to seal a puncture site.

U.S. Pat. No. 5,354,271 to Voda discloses suture threads with barbed ends, wherein the suture threads are deployed into a vessel and then the barbed ends penetrate through the vessel wall and expand to prevent retraction thereof back into the vessel. The suture threads are then tied or otherwise secured across the puncture site.

U.S. Pat. No. 5,324,306 discloses a mass of hemostatic material pushed against the outside wall of a vessel at a puncture site. Manual pressure is applied to ensure blood flow has stopped.

U.S. Pat. No. 5,868,778 discloses a balloon used in combination with a procoagulant injected at the puncture site in order to seal a puncture site of a vessel.

U.S. Pat. No. 5,792,152 discloses a flexible needle with suture attached thereto that is deployed across a puncture site of a vessel. The flexible needle and suture are introduced into the vessel via an entry lumen, proceed through a U-shaped return lumen, and exit the vessel through an exit lumen. Thereafter the suture is drawn further outward from the vessel and tied or otherwise secured across the puncture site.

U.S. Patent Publication No. 2004/0006352 discloses an arterial closure device comprising an assembly in which clasp arms, to which a suture is initially secured, are deployed within a vessel. Penetrating members including suture catches are then separately deployed to snag or capture the sutures associated with a respective clasp arm. The sutures are then pulled taught by pulling the penetrating member with suture catches out from the vessel, and then tied or otherwise secured to close the puncture site. Thereafter the assembly is withdrawn from the body.

Current vessel closure devices thus tend to provide vessel wound closure devices and techniques after an interventional procedure has been performed. A need exists therefore for vessel wound closure systems and methods that apply a vessel wound closure device prior to performance of an interventional procedure within the target vessel.

SUMMARY OF THE INVENTION

The various embodiments described herein comprise vessel wound closure systems and methods for closing a puncture wound in a target vessel. The vessel wound closure system generally comprises at least a biocompatible/biodegradable, viscoelastic self-sealing septum material disposed onto the adventitia of a target vessel prior to performance of an interventional procedure within the target vessel. The septum material may be disposed directly onto the adventitia of the target vessel, or may be disposed within a balloon comprised of natural or bio-degradable polymeric materials of sufficient porosity that permits slow dispersion of the septum material therefrom to adhere to the adventitia of the target vessel. The septum material disposed on the adventitia of the target vessel may further be preformed and comprise a hemostatic valve incorporated therein that closes and seals the vessel wound after an interventional procedure has been performed within the target vessel.

In some embodiments of the vessel wound closure system, access to the target vessel is obtained by piercing or cutting through the skin, followed by blunt dissection to the adventitia, or outer wall, of the target vessel. The septum material is thereafter injected onto the adventitia of the target vessel or into a balloon in proximity to the adventitia from which balloon the septum material seeps to adhere to the adventitia. An introducer is inserted into the target vessel through the septum material, through which introducer various instruments are passed to perform an interventional procedure. After completion of the interventional procedure, the various instruments and the introducer or other components are removed and the septum material remains to seal the vessel wound.

Alternatively, blunt dissection to the adventitia of the target vessel may be omitted where the septum material is injected through a needle having holes aligned to dispose the septum material onto the adventitia of the target vessel. An interventional procedure is then performed through an introducer that has been inserted through the septum material and into the target vessel. After completion of the interventional procedure, the various instruments associated therewith and the introducer or other components are removed while the septum material remains and closes to seal the puncture wound of the target vessel.

In other embodiments, septum material is preformed and disposed on the adventitia of the target vessel prior to performance of an interventional procedure within the target vessel. An introducer is inserted through the preformed septum material and into the target vessel. Various instruments are passed through the introducer to perform the interventional procedure. After the interventional procedure is complete, the various instruments, the introducer, and other components are removed and the preformed septum material remains and closes to seal the puncture wound of the target vessel. The preformed septum material may further comprise a hemostatic valve incorporated therein through which the introducer or other components are disposed to accommodate performance of the interventional procedure.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

As used herein the term proximal, or variants thereof, is understood as closest to a medical practitioner operator, and the term distal, or variants thereof, is understood as furthest from a medical practitioner operator.

Figure 1:
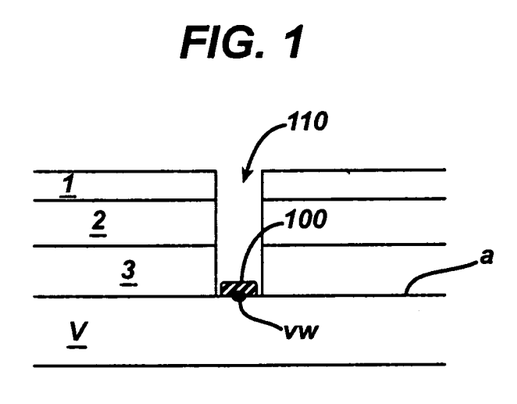
FIG. 1 schematically illustrates a biocompatible/biodegradable, viscoelastic, septum material disposed onto the adventitia of a target vessel to close a vessel wound according to the description herein.

FIG. 1 illustrates generally a biocompatible/biodegradable, viscoelastic, self-sealing septum material 100 disposed onto the adventitia (a) of a target vessel (V) to close a vessel wound (vw) after performance of an interventional procedure in a target vessel (V) according to the description herein. The septum material 100 is disposed onto the adventitia prior to performance of an interventional procedure within the target vessel (V). Various systems and techniques may be used to dispose the septum material 100 onto the adventitia (a) of the target vessel (V), as will be described in greater detail below. The septum material 100 is a biocompatible/biodegradable, viscoelastic, self-sealing material and may be comprised of degradable polyesters, degradable PEG-esters (e.g., poly(ethylene glycol)-initiated lactones such as caprolactone, glycolide, lactide, p-dioxanone, and trimethylene carbonate, and copolymers thereof), degradable polyurethanes, or poly(vinylpyrrolidinone) based functional polymers, for example. Of course, other known or later developed biocompatible/biodegradable, viscoelastic, self-sealing materials may be used to comprise the septum material 100 provided it accommodates the closure of the vessel wound as otherwise described herein.

FIGS. 2-6 illustrate an embodiment of a vessel wound closure system and method wherein the septum material 100 is disposed onto the adventitia (a) of a target vessel (V) prior to performance of an interventional procedure within the target vessel (V).

Figure 2:
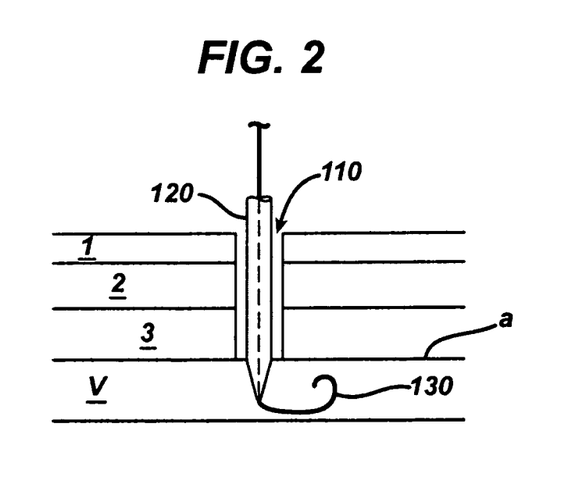
FIG. 2 illustrates a needle and guidewire penetrating. into the target vessel prior to performance of an interventional procedure according to the description herein.
Figure 3:
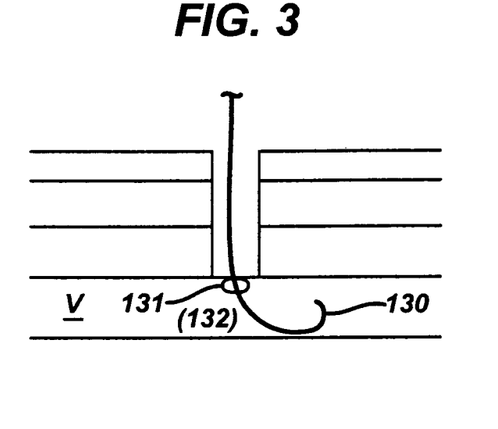
FIG. 3 illustrates the guidewire in place after removal of the needle of FIG. 2 according to the description herein.
Figure 3A:
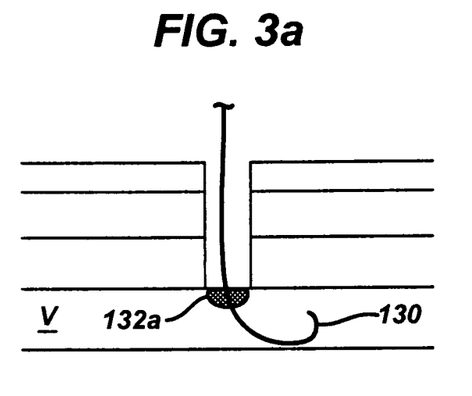
FIGS. 3a and 3b illustrate various guidewire anchors according to the description herein.
Figure 3B:
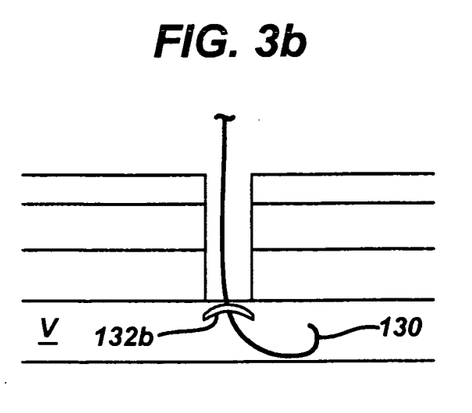

In particular, FIG. 2 illustrates a tissue tract 110 created by piercing or cutting through the skin layers (epidermis 1, dermis 2 and subcutaneous 3), followed by blunt dissection to the adventitia (a) of the target vessel (V). In practice, a first needle 120 may be inserted through the tissue tract 110 and into the target vessel (V) to locate the target vessel (V). Thereafter, a guidewire 130 is inserted through the first needle 120 and into the target vessel (V). Next, as illustrated in FIG. 3, the first needle 120 is removed and the guidewire 130 remains in place within the target vessel (V). The guidewire 130 preferably comprises an expandable member, such as a balloon 131, or other anchor 132 (FIGS. 3a & 3b), that is held against an inside surface of the target vessel (V) during blunt dissection. The guidewire anchor 132 may instead comprise a nitinol mesh 132a or nitinol anchor 132b, for example, that is held against an inside surface of the target vessel (V) during blunt dissection, as in FIGS. 3a and 3b, respectively.

Figure 4:
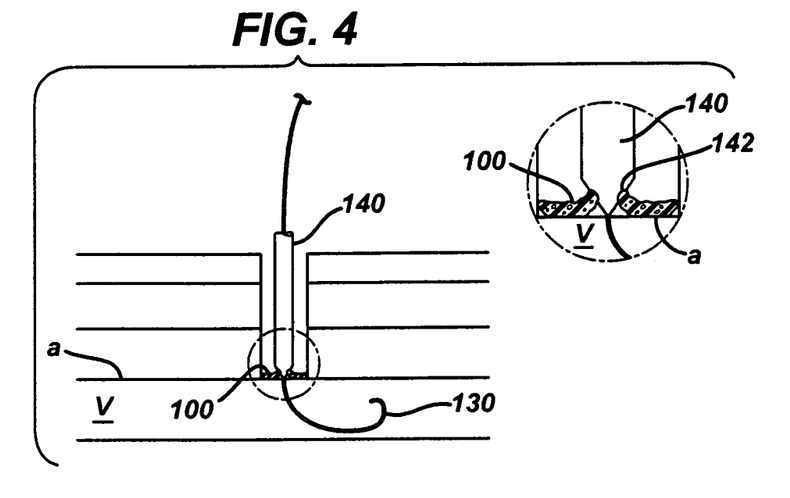
FIG. 4 illustrates disposition of septum material onto the adventitia of the target vessel according to the description herein.

FIG. 4 illustrates the disposition of the septum material 100 onto the adventitia (a) of the target vessel (V). In particular, FIG. 4 illustrates a second needle 140 inserted over the guidewire 130 such that a distal tip 141 of the second needle 140 abuts, but does not enter, the target vessel (V). Septum material 100 may then be injected through the second needle 140 and onto the adventitia (a) of the target vessel (V) through holes 142 (see FIG. 4 inset). After disposition of the septum material 100, the second needle 140 is then removed and an introducer 150 is inserted through the septum material 100 and into the target vessel (V) for performance of the interventional procedure as described further with respect to FIGS. 5 & 6 further below.

Figure 2A:
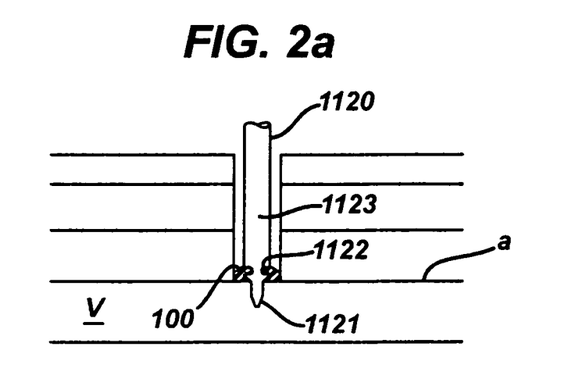
FIG. 2a illustrates a stepped needle penetrating into the target vessel prior to performance of an interventional procedure according to the description herein.

Alternatively, the first needle 120 could instead be a stepped needle 1120 as shown in FIG. 2a and the septum material 100 could be injected onto the adventitia (a) of the target vessel (V) through holes 1122 provided on a portion of the stepped needle 1120. In practice, the target vessel could be located with the stepped, or graduated, needle 1120 (FIG. 2a) rather than the needle 120 and guidewire 130 configuration otherwise depicted in FIGS. 2-6. Blunt dissection may not be necessary where the stepped needle 1120 locates the target vessel (V) and delivers the septum material 100 to the adventitia (a) of the target vessel (V). The smaller diametered portion at the distal end 1121 of the stepped needle 1120 helps insertion of the needle 1120 into the target vessel (V). The smaller diametered distal tip 1121 steps, or graduates, to a larger diametered portion 1123 that abuts the adventitia (a) of the target vessel (V) and resists entry thereinto the target vessel (V). Ideally, the larger diametered portion 1123 of the needle 1120 includes holes 1122 through which septum material may be delivered onto the adventitia (a) of the target vessel (V). After the septum material is injected through the needle 1120 and onto the adventitia (a) of the target vessel (V) through holes 1122, the needle 1120 is removed, leaving the septum material 100 in place. A guidewire 130 and introducer 150 are inserted into and removed from the target vessel to accommodate performance and completion of the interventional procedure as otherwise described above with respect to FIGS. 5 and 6, for example.

Figure 4A:
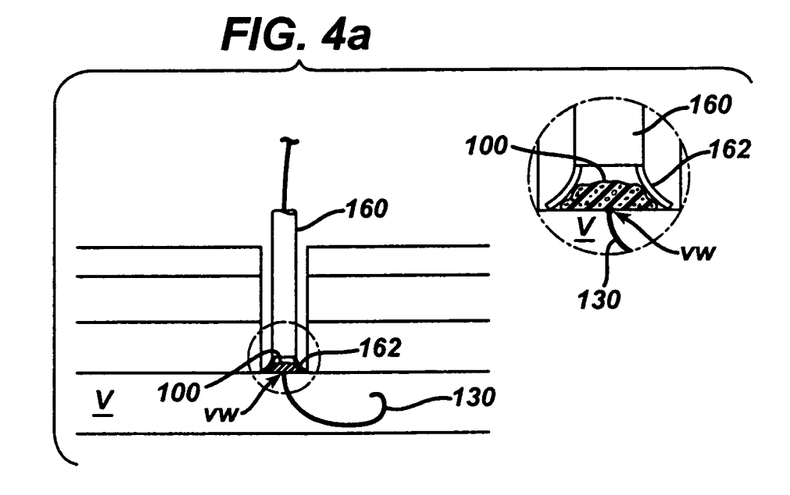
FIGS. 4a-4c illustrate various other techniques of disposing septum material onto the adventitia of the target vessel according to the description herein.
Figure 4B:
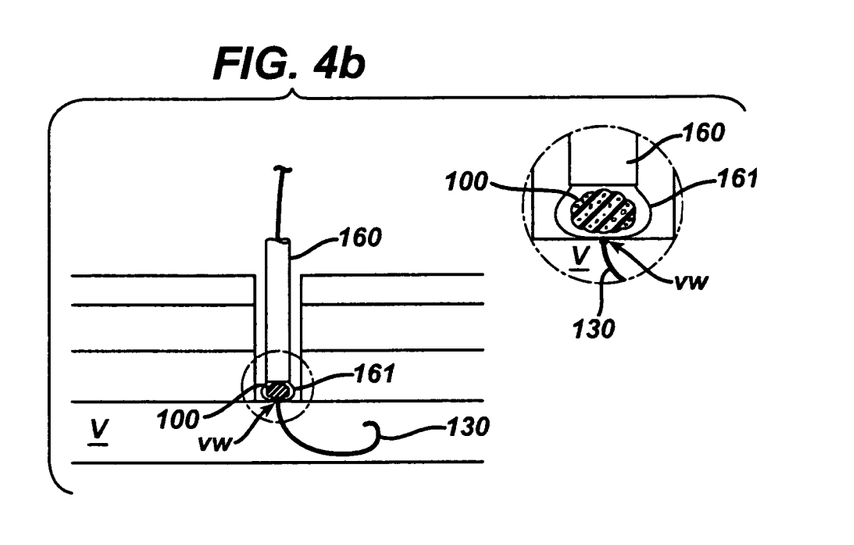
Figure 4C:
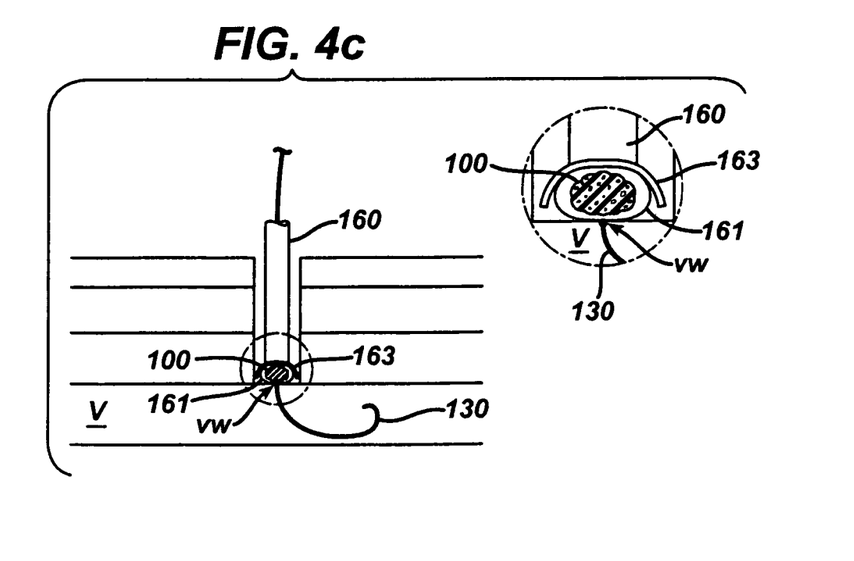

Still further alternatively, as shown in FIGS. 4a-4c, disposition of the septum material 100 may occur through a catheter 160 delivery tool, rather than through a needle as described above. The catheter 160 delivery tool comprises a balloon 161 or rigid prongs 162 deployable from a distal end thereof. The catheter 160 is inserted over the previously inserted guidewire 130. The guidewire 130 may be inserted through needle 120, for example, as described above with respect to FIGS. 2-3. The balloon 161 or prongs 162 deploy at the distal end of the catheter 160 to help dissect tissue further from the site of the vessel wound (vw) at the adventitia (a) of the target vessel (V). Septum material is then injected through the catheter 160 and onto the adventitia (a) of the target vessel (V) or into the balloon 161. The balloon 161 is preferably comprised of a natural material such as intestine or a bio-degradable polymer whose porosity permits the septum material 100 to slowly seep therethrough and adhere to the adventitia (a) of the target vessel (V). Of course, such a natural or biodegradable polymer balloon 161 could be used with various of the systems and methods described herein to help contain the septum material 100 when disposed onto the adventitia (a) of the target vessel (V).

A mold 163 (FIG. 4c) may further be provided at the distal end of the catheter 160 to help contain and form the septum material 100 when disposed through the catheter to the site of the vessel wound (vw). After the septum material 100 is disposed onto the adventitia (a) of the target vessel (V), the catheter 160 is removed while the septum material 100, or balloon 161 containing the septum material 100, remains.

Yet further alternatively, the septum material 100 may be injected onto the adventitia (a) of the target vessel (V) by a syringe (not shown) as the artisan should readily appreciate, rather than through any of the septum material delivery tools otherwise described herein.

Figure 5:
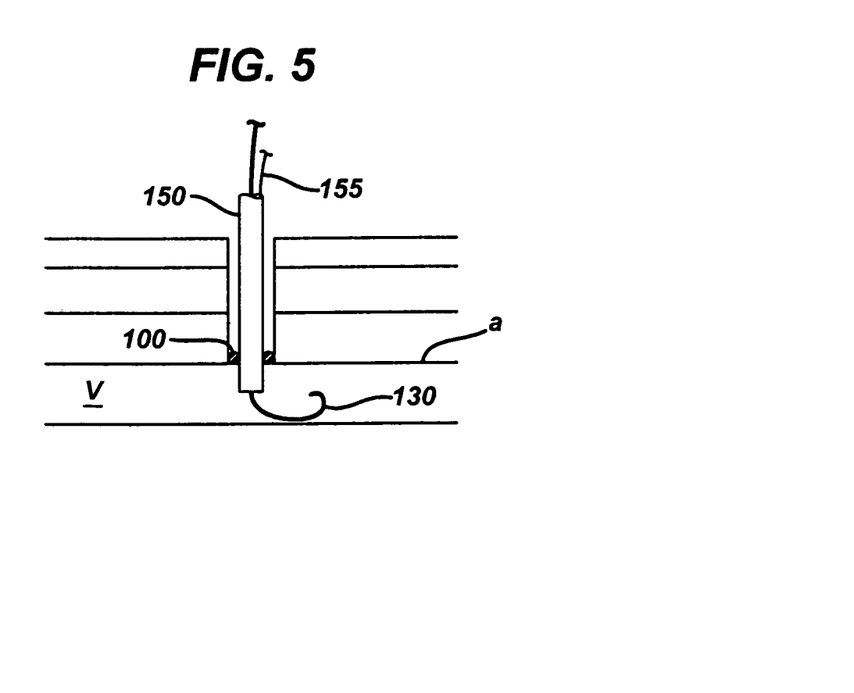
FIG. 5 illustrates insertion of an introducer over the guidewire, through the septum material, and into the target vessel according to the description herein.

FIG. 5 illustrates an introducer 150 inserted over the guidewire 130. and into the target vessel (V) after the septum material 100 has been disposed onto the adventitia (a) and any septum material delivery tool, i.e., the first needle 120, the syringe, the second needle 140, or the catheter 160, as the case may be, has been removed. A dilator 155 may precede insertion of the introducer 150 in conventional manner if desired, in order to aid the insertion of the introducer 150 through the tissue tract 110, the septum material 100 and into the target vessel (V). If used, the dilator 155 may be removed after the introducer 150 has penetrated into the target vessel (V). Once the introducer 150 is inserted, then various instruments may be inserted therethrough and an interventional procedure within the target vessel (V) is performed.

Figure 6:
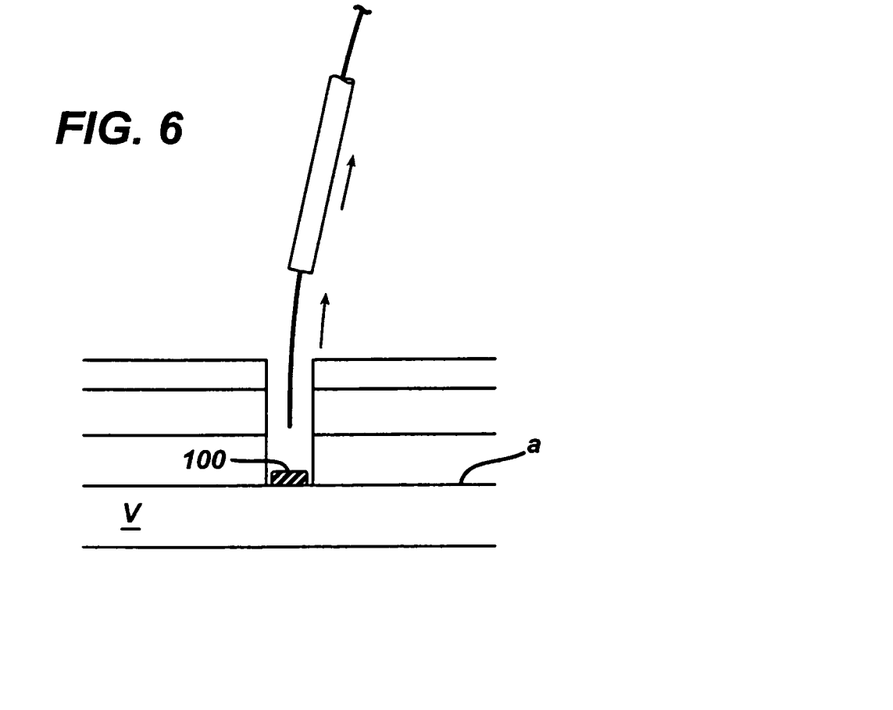
FIG. 6 illustrates removal of the introducer, any instruments, and the guidewire as the septum material closes the vessel wound according to the description herein.

Upon completion of the interventional procedure, as shown in FIG. 6, the various instruments, the introducer 150, and the guidewire 130 are removed from the target vessel (V) through the septum material 100, which remains in place on the adventitia (a) of the target vessel. Because of the viscoelasticity properties of the septum material 100, which ideally exhibits at least 800-900% deformation, the septum material 100 readily recovers to close and seal the opening through which the introducer 150 and guidewire 130 were emplaced during the interventional procedure.

FIGS. 7-11 illustrate another embodiment of a vessel wound closure system and method wherein the septum material 100 is preformed and disposed onto the adventitia (a) of a target vessel (V) prior to performance of an interventional procedure within the target vessel (V), wherein like reference numerals or characters are used to refer to like parts. The preformed septum material 100 may include a hemostatic valve 101 incorporated therein, through which valve an introducer 150 or other instruments are passed through and into the target vessel (V) to perform an interventional procedure within the target vessel (V). After completion of the interventional procedure, the introducer 150 and other instruments are removed through the valve 101, which closes and seals the vessel wound (vw).

Figure 7:
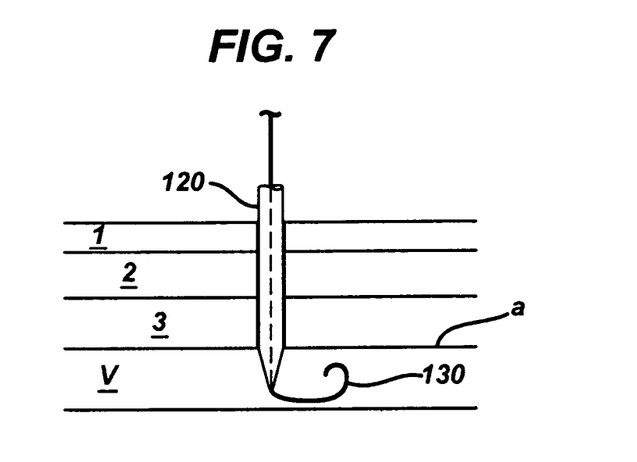
FIG. 7 illustrates a first needle and a guidewire penetrating into the target vessel prior to an interventional procedure according to the description herein.
Figure 8:
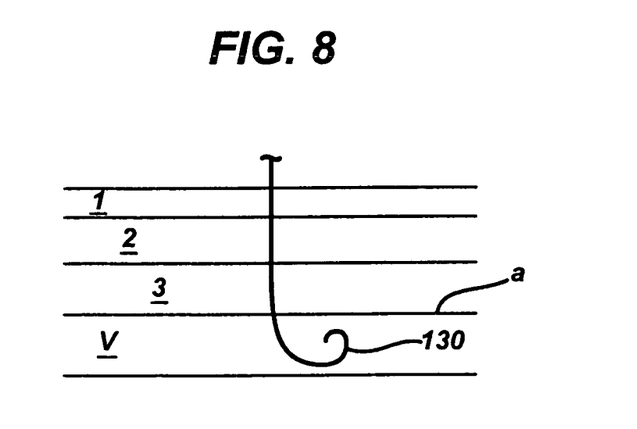
FIG. 8 illustrates the guidewire in place after removal of the first needle of FIG. 7 according to the description herein.

In particular, FIG. 7 illustrates a first needle 120 that locates the target vessel (V) by penetrating through the skin and into the target vessel (V). A guidewire 130 is then inserted through the first needle 120 and into the target vessel (V). Thereafter, as shown in FIG. 8, the first needle 120 is removed, leaving only the guidewire 130 in place within the target vessel (V).

Figure 9:
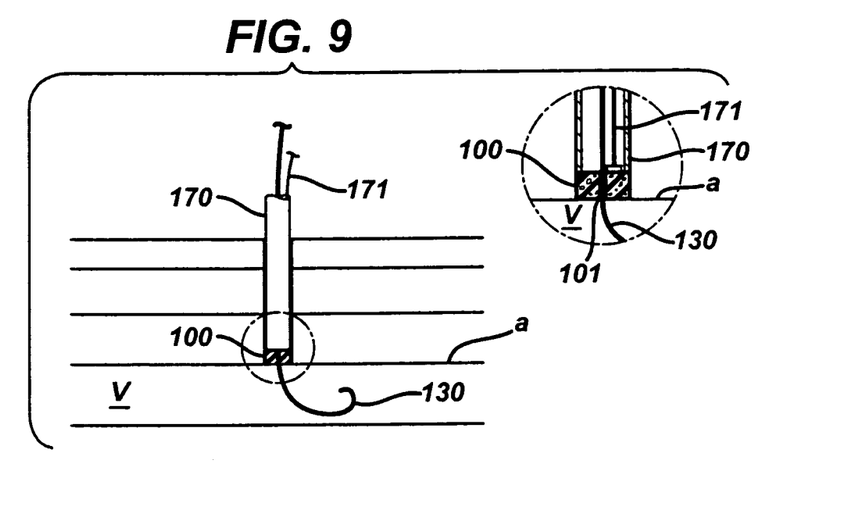
FIG. 9 illustrates disposition of preformed septum material onto the adventitia of a target vessel according to the description herein.

FIG. 9 illustrates the disposition of the preformed septum material 100 onto the adventitia (a) of the target vessel (V). In particular, FIG. 9 illustrates a catheter 170 inserted over the guidewire 130 such that a distal end of the catheter 170 approaches, but does not enter, the target vessel (V). The preformed septum material 100 is then pushed through the catheter 170 and onto the adventitia (a) of the target vessel (V) (see FIG. 9 inset). Preferably, a biocompatible/biodegradable bonding agent is applied to one or both of the distal surface of the preformed septum material 100 and the exposed adventitia surface to aid adherence of the preformed septum material 100 thereto the adventitia (a) when disposed thereon from the catheter 170. Of course, the preformed septum material 100 could be contained within a balloon 161, as described above with respect to FIGS. 4a-4c, in which case the septum materials seeps slowly out from the balloon 161 and adheres to the adventitia. A pusher 171 may be provided through the catheter to aid in disposing the preformed septum material 100 onto the adventitia. In any case, after the preformed septum material 100 is disposed onto the adventitia, the catheter 170 and the pusher 171, if used, are removed.

Although the preformed septum material 100 may be penetrated to access the target vessel (V), it is preferable to provide the preformed septum material with a hemostatic valve 101, through which the introducer 150, the guidewire 130, or other instruments may access the target vessel (V).

Figure 10:
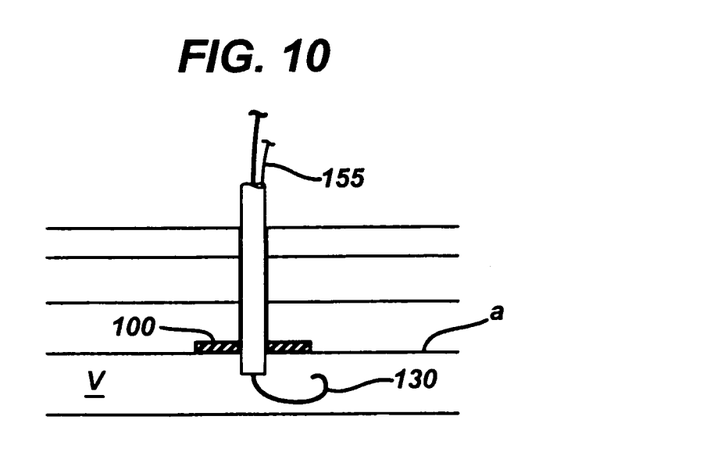
FIG. 10 illustrates insertion of an introducer over the guidewire, through the preformed septum material, and into the target vessel according to the description herein.

FIG. 10 illustrates an introducer 150 inserted over the guidewire 130 and into the target vessel (V) through the valve 101 of the preformed septum material 100 after the preformed septum material 100 has been disposed onto the adventitia (a) and the catheter 170 has been removed. As in earlier described embodiments, a dilator 155 may precede insertion of the introducer 150 in conventional manner if desired, in order to aid the insertion of the introducer 150 through the valve 101 and the septum material 100, and into the target vessel (V). If used, the dilator 155 may be removed after the introducer 150 has penetrated into the target vessel (V). Once the introducer 150 is inserted, then various instruments may be inserted therethrough and an interventional procedure within the target vessel (V) is performed.

Figure 11:
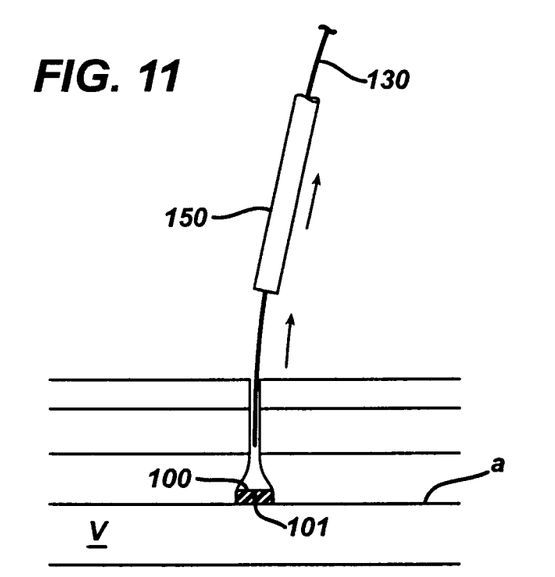
FIG. 11 illustrates removal of the introducer, any instruments, and the guidewire as the septum material closes the vessel wound according to the description herein.

Upon completion of the interventional procedure, as shown in FIG. 11, the various instruments, the introducer 150, and the guidewire 130 are removed from the target vessel (V) through the valve 101 and the septum material 100, which. remain in place on the adventitia (a) of the target vessel. Due to the valve 101 and the viscoelastic properties of the septum material 100, the access hole into the target vessel (V) is readily closed and sealed.

The various exemplary embodiments of the invention as described hereinabove do not limit different embodiments of the systems and methods of the invention. The materials described herein are not limited to the materials, designs or shapes referenced herein for illustrative purposes only, and may comprise various other materials, designs or shapes suitable for the systems and methods described herein, as should be appreciated by the artisan.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A vessel wound closure system used prior to performance of an interventional procedure in a target vessel, comprising:
   a self-sealing septum material adapted to be disposed onto adventitia of the target vessel; and
   a stepped needle comprising a smaller diametered distal portion and a larger diametered proximal portion, the smaller diametered portion comprising a pointed tip configured to pierce through the adventitia of the target vessel to allow the larger diametered portion to externally abut the adventitia of the target vessel, the larger diametered portion comprising at least one opening formed in a side wall thereof, through which the self-sealing septum material is disposed onto the adventitia of the target vessel.

2. The vessel wound closure system of claim 1, wherein the self-sealing septum material is a biocompatible/biodegradable, viscoelastic material.

3. The vessel wound closure system of claim 2, wherein the self-sealing septum material exhibits at least 800-900% deformation properties that close and seal access holes provided therein to accommodate performance of the interventional procedure.

4. The vessel wound closure system of claim 3, further comprising a balloon in which the self-sealing septum material is contained and from which the self-sealing septum material seeps onto the adventitia of the target vessel.

5. The vessel wound closure system of claim 4, wherein the balloon is comprised of a natural membrane or a biodegradable polymeric membrane of sufficient porosity to permit seepage of the self-sealing septum material onto the adventitia of the target vessel.

6. The vessel wound closure system of claim 3, wherein the self-sealing septum material is preformed to accommodate disposition thereof onto the adventitia of the target vessel at the vessel wound.

7. The vessel wound closure system of claim 6, wherein the preformed self-sealing septum material further comprises a hemostatic valve incorporated therein and permitting access therethrough and closure thereof.

8. The vessel wound closure system of claim 6, further comprising a bonding agent applied to one or both of the preformed self-sealing septum material and the adventitia of the target vessel to secure the preformed self-sealing septum material onto the adventitia.

9. The vessel wound closure system of claim 1, further comprising:
- a guidewire adapted to be inserted through the stepped needle and into the target vessel; and
- an introducer inserted over the guidewire and into the target vessel, through which an interventional procedure is performed.

10. The vessel wound closure system of claim 9, wherein the guidewire further comprises an anchor at a distal end thereof that abuts against an inside surface of the target vessel when deployed.

11. The vessel wound closure system of claim 10, wherein the anchor comprises a nitinol mesh or basket.

12. The vessel wound closure system of claim 11, wherein the anchor comprises a balloon.

* * * * *